United States Patent [19]

Hawke et al.

[11] Patent Number: 5,049,507

[45] Date of Patent: Sep. 17, 1991

[54] METHOD OF C-TERMINAL PEPTIDE SEQUENCING

[75] Inventors: David H. Hawke, Hayward; Victoria L. Boyd, San Carlos, both of Calif.

[73] Assignee: Applied Biosystems, Inc., Foster City, Calif.

[21] Appl. No.: 454,666

[22] Filed: Dec. 21, 1989

[51] Int. Cl.$^5$ .......................................... G01N 33/68
[52] U.S. Cl. ...................................... 436/89; 530/345; 530/402
[58] Field of Search .................. 436/89; 530/345, 402, 530/407–410

[56] References Cited

U.S. PATENT DOCUMENTS

| 4,837,165 | 6/1989 | Hawke | 530/345 X |
| 4,935,494 | 6/1990 | Miller | 436/89 X |

FOREIGN PATENT DOCUMENTS

| 0217634A2 | 4/1987 | European Pat. Off. | |
| 1250863 | 10/1989 | Japan | 436/89 |

OTHER PUBLICATIONS

Stark, Biochemistry, vol. 7, No. 5, pp. 1796–1807, 1968.
Cromwell et al, Biochemistry, vol. 8, No. 12, pp. 4735–4740, 1969.
Laursen et al, Methods of Biochemical Analysis, vol. 26, pp. 201–202 & 268–272, 1980.
Rangarajan, M., in "Protein/Peptide Sequence Analysis: Current Methodologies" (1988) Chapter 7, pp. 135–144, A. S. Bhown, Ed.
Miller, C. G., et al., "Studies on the Use of Silyl Compounds for Protein Carboxy-Terminal Sequence Analysis" (1989), Techniques in Protein Chemistry, Ed. T. E. Hugh, Academic Press, pp. 67–78.
Tarr, G. E., in Methods in Protein Sequence Analysis (1988), Section 4.1: The Long Search for a Viable Method of C–Terminal Sequencing, pp. 129–151, Ed. B. Wittmann-Leibold, Proceedings of the 7th Intern'l Conf., Berlin.
Hawke, D. H., et al., Microsequence Analysis of Peptides and Proteins: Trimethylsilylisothiocyanate as a Reagent for COOH–Terminal Sequence Analysis (1987), Analytical Biochem. 166 pp. 298–307.
Parham, M. E., et al., "Carboxyl–terminal Sequential Degradation" (1978), Biochem. Biophys. Res. Comm. vol. 80, pp. 1–6.
Kenner, G. W., et al., in Peptides. Part IV. "Selective Removal of the C–Terminal Residue as a Thiolhydantoin, The Use of Diphenyl Phosphorisothiocyanatidate" (1953) J. Chem. Soc.
Stark, G. R., in Methods in Enzymology, "Sequential Degradation of Peptides and Proteins from their COOH Termini with Ammonium Thiocyanate and Acetic Anhydride" (1972), C. H. W. Hirs, et al., Eds., vol. 25, p. 369, Academic Press.
Miller, M. J., et al., "The Chemistry of a Method for the Determination of Carboxyl–terminal Residues in Peptides" (1987), J. Org. Chem. vol. 42, pp. 1750–1761.
Meuth, J. L., et al., "Stepwise Sequence Determination from the Carboxyl Terminus of Peptides" (1982), Biochemistry vol. 16, pp. 3750–3757.
Parham, M. E., et al., "A New Method of Determination of the Carboxyl–terminal Residue of Peptides" (1978), Biochem. Biophys. Res. Comm. vol. 80, pp. 7–13.

Primary Examiner—Robert J. Hill, Jr.
Attorney, Agent, or Firm—Joseph Smith; Peter J. Dehlinger

[57] ABSTRACT

A method of C-terminal peptide sequencing. The peptide is reacted with a mixed anhydride of isothiocyanic acid and a carboxylic, carbonic, or sulfonic acid, under basic conditions, to produce a C-terminal peptidyl thiohydantoin. The C-terminal amino acid can be identified by cleaving the thiohydantoin from the peptide and identifying the free amino acid thiohydantoin.

13 Claims, 8 Drawing Sheets

(I)

(II)

(III)

(IV)

(V)

(I)

(II)

(III)

METHOD OF C-TERMINAL PEPTIDE SEQUENCING

FIELD OF THE INVENTION

The present invention relates to a method for determining the C-terminal amino acid of a peptide, and for sequencing a peptide from its C-terminal peptide end, and to a reagent useful in such methods.

REFERENCES

Cromwell, L. D., et al., Biochemistry 8:4735 (1969).
Edman, P., Acta Chem Scand, 4:277 (1950).
Hawke, D. H., et al, Anal Biochem, 166:298 (1987).
Kenner, G. W., et al., J Chem Soc, 673 (1953).
Meuth, J. L., et al., Biochemistry, 16:3750 (1982).
Miller, M. J., et al, J Org Chem, 42:1750 (1977).
Miller, C. G., et al, in "Techniques in Protein Chemistry (Hugh, T. E., ed), Academic Press, pp. 67–78 (1989).
Miller, C. G., et al., Abstract T188 from the Third Symposium of the Protein Society, Seattle Wash. (July 29–Aug. 2, 1989).
Parham, M. E., et al, Biochem Biophys Res Commun, 80:7 (1978).
Rangarajan, M, in "Protein/Peptide Sequence Analysis: Current Methodologies" (Bhown, A. S., ed), CRC Press, pp 136–144 (1988).
Schlesinger, D. H., et al, Anal Biochem, 95:494 (1979).
Shively, J. E., et al, TIBS 14:246 (1989).
Stark, G. R., in *Methods in Enzymology* (Hirs, C. H. W., et al, eds.), Vol 25, p 369 Academic Press (1972).
Tarr, G. E., in "Methods in Protein Sequence Analysis", (Whittmann-Liebold, B., ed) Springer Verlag, pp. 129–151 (1988).

BACKGROUND OF THE INVENTION

Determining the amino acid sequence, i.e., primary structure, of a peptide is central to understanding the structure of the peptide, as well as to manipulating the peptide to achieve desired properties in a modified or altered form. In addition, the amino acid sequence of a peptide is useful in a variety of recombinant DNA procedures for identifying the gene coding sequence of the peptide, for producing the peptide recombinantly, and/or for producing site-specific modifications of the peptide.

Early attempts to determine the amino acid sequence of peptides relied on acid hydrolysis of the peptide or enzymatic degradation to separate the peptide into its component amino acids. Both of these methods were slow and produced complicated mixtures of amino acids which then had to be separated for analysis.

The development of reagents to sequence peptides by more systematic means greatly facilitated the determination of amino acid sequences. The most widely used method involves reacting the N-terminus of the peptide with phenyl isothiocyanate (PITC), a process known as Edman degradation (Edman). Reaction of PITC with the free terminal amino group adds a phenylthiourea group, which cyclizes to form a free anilinothiothiazolinone (ATZ) of the N-terminal amino acid, and a shortened peptide. The ATZ-derivative of the N-terminal amino acid is extracted, converted to the corresponding phenylthiothiohydantoin (PTH) which is then analyzed by HPLC. The amino-acid-PTH derivatives produced in the Edman reaction are racemized in the course of the Edman reaction, and thus the reaction cannot be used to distinguish L- and D-form amino acids.

N-terminal sequencing is carried out by successively converting the next-in N-terminal amino acid to the free amino acid PTH, and identifying each successively released amino acid. The method is generally reliable for N-terminal sequences up to about 20–40 or more amino acid residues.

Despite the relative ease and reliability of N-terminal sequencing methods, it is often desired to obtain C-terminal amino acid sequence information which may be inaccessible or only obtained with difficulty by this method. Information about the carboxy terminal sequence may be useful for certain types of recombinant DNA procedures, particularly since the C-terminal end of the coding region of a protein corresponds to the end closest to a poly A tail, which is likely to be present in cDNA clones.

Three general approaches have been proposed for C-terminals peptide sequencing: enzymatic, physical, and chemical. The enzymatic strategy, which involves analyzing the products resulting from treatment of the peptide with carboxypeptidase over time, is limited by the difficulty of controlling the extent of carboxypeptidase cleavage. Typically, the identification of the next-in amino acid becomes difficult after 3–5-residues have been cleaved.

The most common physical tools used for C-terminal sequencing are fast atom bombardment mass spectrometry (FAB/MS), and nuclear magnetic resonance (NMR) spectroscopy. FAB/MS analysis is applicable to 1–10 nmole amounts of peptide, but requires expensive mass spectrometry equipment. NMR analysis requires relatively large amounts of peptides, typically in the $\mu$molar range, and also involves relatively expensive equipment.

In view of the limitations of enzymatic and physical approaches to C-terminal sequencing, considerable effort has been invested in developing chemical methods for determining C-terminal amino acids residues, and for C-terminal sequencing. An inherent difficulty in C-terminal sequencing is the relatively poor reactivity of the carboxyl group, in contrast to the relative ease of addition at the N-terminal amino group. Of the reaction methods which have been proposed for C-terminal sequencing, three have received special attention.

The first activation method involves generating a carboxyamido derivative at the C-terminal end of the peptide, followed by reaction with bis(I,I-trifluoroacetoxy)iodobenzen to form a derivative which rearranges and hydrolyses to a shortened carboxyamidopeptide and the aldehyde derivative of the C-terminal amino acid (Parham). The method has been successfully carried out only to 3–6 cycles before the reaction halts. In a second, related approach, the carboxy terminus is reacted with pivaloylhydroxamide to effect a Lossen rearrangement. One limitation of the method is that the chemistry does not degrade aspartic and glutamic acid residues (Miller, 1977).

The most widely studied of the C-terminal chemistries is the thiohydantoin (TH) reaction. In one general method for carrying out the TH method, the carboxyl group is activated with an anhydride, such as acetic anhydride, in the presence of an ITC salt or acid, to form a C-terminal peptidyl-TH via a C-terminal ITC intermediate (Stark, 1972). The peptidyl-TH can be cleaved to produce a shortened peptide and a C-terminal amino acid TH, which can be identified, e.g., by high pressure liquid chromatography (HPLC). The coupling conditions in this method typically require about 90 minutes at 60°–70° C. (Meuth), and often lead to degradation of some of the amino acid side chains in the peptide. Further, the anhydride reagent is relatively unstable, and therefore presents storage problems.

A C-terminal TH sequencing method which can be carried out under milder conditions has been described by the inventor and co-workers (Hawke). Using trimethylsilyl ITC (TMS-ITC) as the reagent, TH formation was achieved by activation of the peptide with acetic anhydride for 15 min at 50° C., followed by reaction with TMS-ITC for an additional 30 min at 50° C. The method suffers from the disadvantage, noted above, of peptide exposure to a highly reactive anhydride activating agent. In addition, and like the related TH-generating methods described above, the TH-amino acid reaction products are racemized, and thus the method cannot be used to distinguish D- and L-form amino acids.

The C-terminal sequencing methods involving TH formation just described have commonly lead to racemized products. A modification of the C-terminal reaction employing phosphoryl isothiocyanatidate reagent has been proposed (Kenner). Although TH was produced, the reaction was too slow to be very useful. Miller et al have proposed a related method, but using a mercaptobenzothiazole derivative. The rationale for using this compound is that cyclization could occur with concommitant opening of the thiazole ring.

SUMMARY OF THE INVENTION

It is one general object of the invention to provide an improved method of determining the C-terminal amino acid residue of a peptide.

It is a more specific object of the invention to provide such a method which is relatively rapid, and can be carried out under relatively mild reaction conditions, and in particular, under conditions which do not involve the use of anhydride activation reagents.

The invention includes, in one aspect, a method for determining the C-terminal amino acid residue of a peptide. The peptide is reacted with a mixed anhydride of isothiocyanic acid and a carboxylic, carbonic or sulfonic acid, under basic conditions, to produce a C-terminal peptidyl thiohydantoin (TH). C-terminal hydrolysis of the peptidyl-TH bond releases the amino acid TH, which can then be identified, e.g., by HPLC, as an amino acid TH adduct.

In one preferred embodiment of the invention, the mixed anhydride reagent used in the method has the form:

where R is an alkyl or aryl group.

Where the method is used for C-terminal sequencing, the peptide is preferably attached to a solid support through an internal or N-terminal amino group. The peptide is subjected to successive rounds of C-terminal TH formation and amino acid TH release.

According to one aspect of the invention, the formation of the TH-peptidyl complex, and subsequent cleavage under acidic conditions preserves the sterochemistry of the C-terminal amino acids. This is evidenced by the presence of only a single TH-amino acid (isoleucine) peak on HPLC, under chromatographic conditions in which diasteriomeric forms of Ile-TH are resolvable as a doublet. Thus the method can be practiced under conditions which permit identification of sterioisomeric forms of C-terminal amino acids.

These and other objects and features of the invention will become more fully apparent when the following detailed description of the invention is read in conjunction with the accompanying drawings.

DETAILED DESCRIPTION OF THE INVENTION

In practicing the method of the invention, a mixed anhydride of isothiocyanic acid and a carboxylic, carbonic or sulfonic acid (Section A) is reacted with the C-terminal residue of a peptide, to form a peptidyl thiohydantoin (Section B). The peptidyl-TH is treated under conditions which cleave the C-terminal amino acid-TH from the peptide and the released compound is identified, for example by HPLC, to determine a C-terminal amino acid (Section C) or for C-terminal peptide sequencing (Section D). Related mixed anhydride compounds which may be used for C-terminal sequencing are also disclosed (Section E).

A. Mixed anhydride Reagent

The reagent employed in the method of the present invention is a mixed anhydride of isothiocyanic acid

Figure 1:
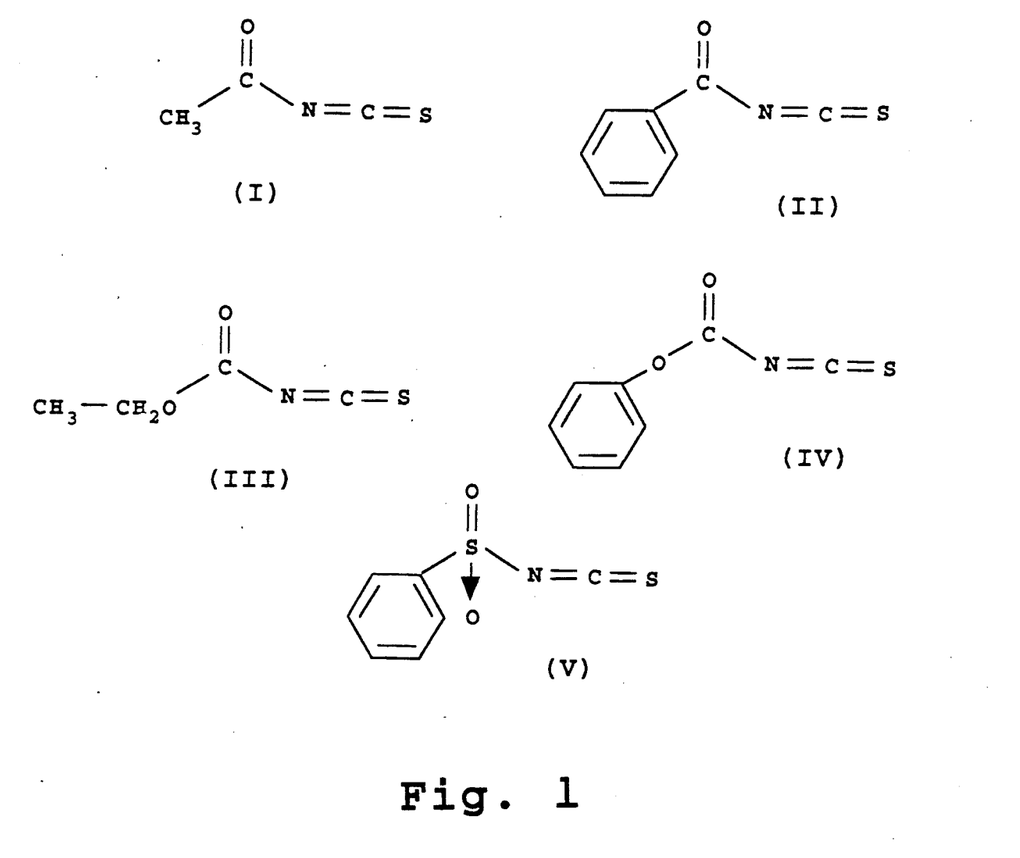
FIG. 1 shows mixed anhydrides of isothiocyanic acid (compounds I-V) which may be used in practicing the present invention.

(ITC) and carboxylic, carbonic, or sulfonic acid. Several exemplary mixed anhydride reagents are illustrated in FIG. 1. These include:

(a) an alkyl or aryl acyl-ITC compound, as exemplified by acetyl ITC (I), and benzoyl ITC (II). The alkyl group may be selected from the group of alkyl and cycloalkyl compounds, such as methyl, ethyl propyl, t-butyl, and related carbon-containing compounds linked to the acyl carbon through a carbon-carbon linkage. The aryl group may be a benzene, substituted benzene, or related compound linked to the acyl carbon through an aryl ring carbon atom. These two classes of compounds are also referred to herein as mixed anhydrides of ITC and carboxylic acids, since hydrolysis at the CO—N bond yields a carboxylic acid and HNCS.

(b) an alkoxy or aryloxy carbonyl-ITC compound, as exemplified by ethoxy acyl-ITC (III), or benzoxy carbonyl-ITC (IV). The ether linked alkyl or aryl groups in the compounds are as described in (a). These two classes of compounds are also referred to herein as mixed anhydrides of isothiocyanic acid and carbonic acids, since hydrolytic cleavage of the compounds produce a carbonic acid ester and HNCS.

(c) an alkyl or aryl sufonyl-ITC compound, as exemplified by benzylsulfonyl-ITC (V). The alkyl or aryl groups are as described in (a). These two classes of compounds are also referred to herein as mixed anhydrides of sulfonic acid and ITC, since hydrolytic cleavage of the compounds produce a sulfonic acid and HNCS.

In one preferred embodiment of the invention, the compound is a mixed anhydride of a carboxylic acid and isothiocyanate, as described in (a), and having the general formula:

where R may be any carbon-containing group, such as an alkyl or aryl group, which allows reagent solubility in the solvent used in the TH-forming reaction, and reactivity toward a peptide acyl group, in the isothiocyanation reaction to be described.

Some compounds in this class may be obtained commercially, or prepared according to known procedures. One method of preparing acyl-substituted ITCs involves dissolving an isothiocyanate in a dry, inert solvent containing a base, and slowly adding the desired acyl chloride. For example, a synthesis of benzoyl ITC employs benzoyl chloride in acetonitrile or dichlormethane or toluene as an inert solvent, and diisopropyl ethyl amine as the base.

Mixed anhydrides of isothiocyanic acid and carbonic acid (ROC(O)NCS) may be formed by analogous methods, using a selected alkyl or aryl ester chloride in reaction with ITC salt. Similarly, mixed anhydrides of isothiocyanic acid and sulfonic acid are formed by reacting the desired benzensulfonyl chloride with an ITC, as outlined in Example 7.

B. Reaction Method to form Peptidyl TH

In practicing the method of the invention, the peptide whose C-terminal amino acid is to identified is reacted with the mixed anhydride reagent reagent under basic conditions in which the C-terminal acid group of the amino acid is deprotonated. The C-terminal amino acid is converted to a C-terminal amino acyl TH which is linked to the next-in C-terminal amino acid in the peptide through a ring-nitrogen amide bond.

As used above, the term "peptide" is intended to include both peptides and proteins, these generally being distinguished by less than or more than 100 amino acids, respectively.

Where the method is used to identify only the C-terminal amino acid residue of the peptide, the peptide may be reacted in free form, i.e., unattached to a solid support, where the amino terminus is protected. Typically, where successive rounds of C-terminal amino acid identification are desired, for purposes of C-terminal sequencing, the peptide is first attached at its N-terminus or internal side chain to a solid support.

Methods for attaching peptides to solid supports, such as activated glass beads, carboxylated or aminated resin beads, and the like are well known. In one preferred approach, employed in the method described in Example 1, the dipeptide Leu-Val was immobilized to aminated resin by a benzyl diisothiocyanate.

The peptide, either in free or immobilized form, is dissolved or suspended in a suitable solvent under basic, preferably non-aqueous conditions effective to deprotonate the C-terminal carboxylic acid group. The solvent preferably also includes pyridine, which may serve an important catalytic role in thiohydantoin (TA) ring formation, as discussed below. One preferred solvent is anhydrous acetonitrile containing 10% anhydrous pyridine. A typically reaction volume is about 100 μL reaction solvent per 1-3 mg peptide.

The mixed-anhydride reagent from above is now added to the peptide suspension, preferably in molar excess of the peptide carboxyl group available for reaction in the reaction suspension. Typically, about 10 μL of the reagent are added per 100 μL reaction solvent.

The TH-forming reaction is preferably carried out at 50°-70° C., for about 10-60 minutes, preferably at about 50° C. for 15-30 minutes, to minimize reaction of the ITC reagent with non-carboxyl groups in the peptide. Following this, the reaction mixture is cooled to room temperature, and the peptidyl TH is recovered. Where the peptide is attached to a solid support, the support recovery is accomplished readily by washing the support, for example, with several volumes of acetonitrile, and drying the washed support, for example, by vacuum centrifugation. Where the peptide is reacted in free form, the peptidyl TH may be recovered by chromatographic separation or the like in a solvent system which does not produce end-terminal cleavage of the amino acid TH from the peptide.

Figure 2:
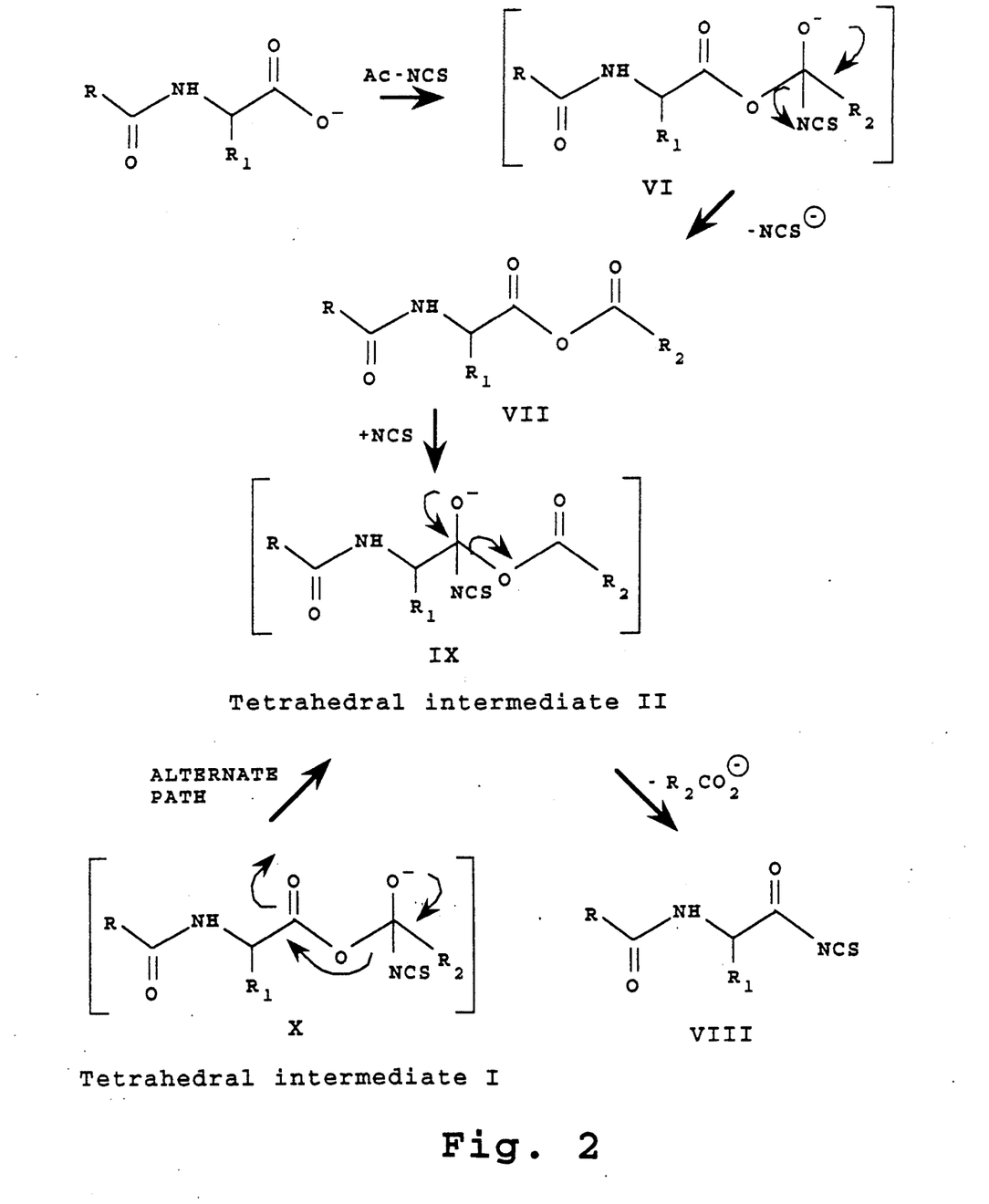
FIG. 2 shows the proposed mechanism of reaction of a peptide carboxyl group with an alkyl acyl ITC reagent, in accordance with the invention, to form a peptidyl ITC compound.
Figure 3:
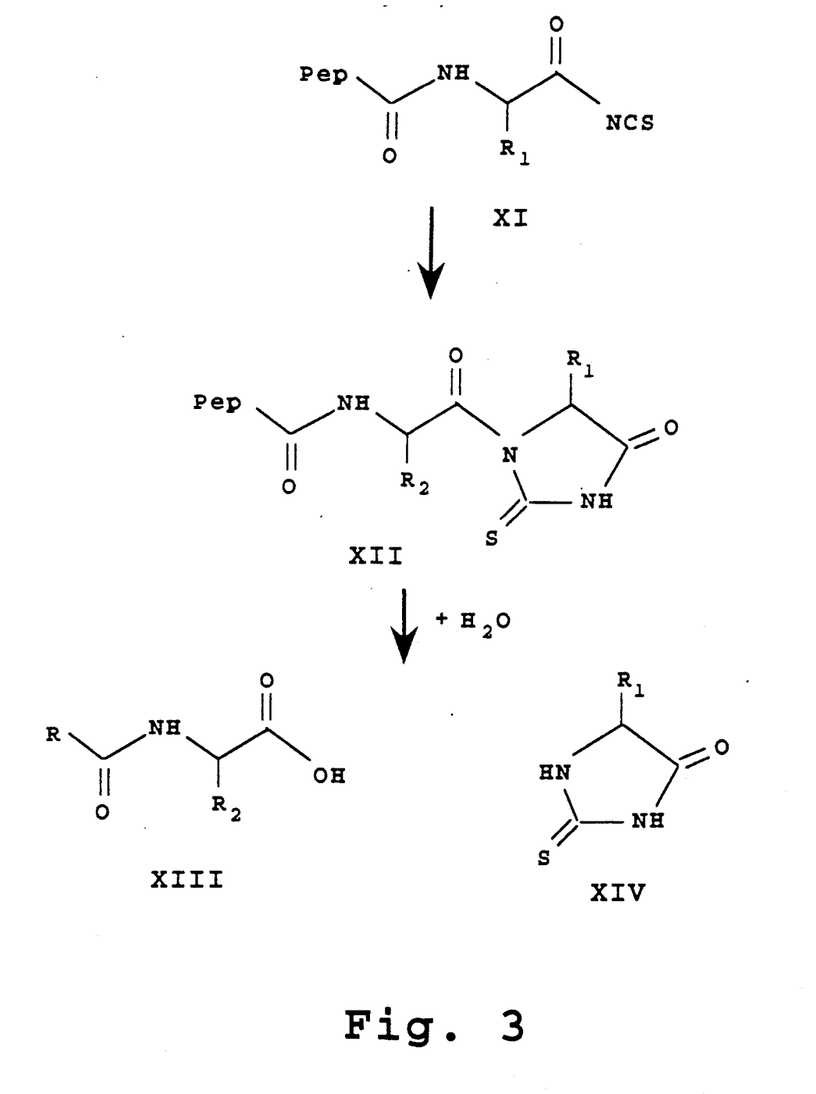
FIG. 3 shows a proposed mechanism of formation of a peptidyl thiohydantoin (TH) and, and hydrolysis of the terminal amino acid TH to form an amino acid TH and a shortened peptide.

FIGS. 2 and 3 show the proposed mechanism of the reaction for peptidyl TH formation in accordance with the method of the invention. In the reaction mechanism shown at the top in FIG. 2, the mixed anhydride reagent VII reacts through an unstable ITC intermediate to form the peptidyl mixed anhydride shown at VI in the figure. The anhydride then reacts with a free thiocyanate ion produced in the anhydride reaction, to form the peptidyl ITC compound shown at VIII in the figure via a tetrahedral intermediate IX. In this proposed mechanism, the mixed anhydride reagent functions both as an activating reagent, to form a reactive peptidyl anhydride, and as a source of thiocyanate ions for reaction with the anhydride.

An alternative reaction mechanism is shown in the second line in FIG. 2. Here the thiocyanate group in the tetrahedral intermediate IX in the figure migrates to the peptide carbonyl carbon, forming the tetrahedral intermediate IX, which rapidly collapses to form the peptide ITC compound shown at VIII.

With continued reference to FIG. 2, there are two possible electrophilic sites of reaction of the peptidyl deprotonated (nucleophilic) oxygen atom. The first site, and the one shown in the FIG. 2 reaction scheme, is the carbonyl carbon. The second site is the the thiocarbonyl carbon, which would lead to the wrong reaction products. Experiments conducted in support of the present invention indicate that more electrophilic substitution at the carbonyl carbon favors reaction at the thiocarbonyl carbon, based on the percentage of the amino acid-TH compound formed. Thus, for example, alkyl and aryl carbonyl groups (the mixed anhydrides of isothiocyanic acid and carboxylic acids) give the highest percentage of the desired TH product, and the more electronegative ester reagents (mixed anhydrides of isothiocyanic acid and carbonic acid), a lower prercentage of the desired product. Under present conditions, the sulfonic acid mixed anhydride reagent gives the lowest percentage of the desired TH product.

The reaction of the peptidyl ITC compound XI to form the desired peptidyl TH is shown in FIG. 3, and presumably involves an electrophilic attack by the thiocyanate carbon on the amide nitrogen in the peptide ITC compound, with rapid cyclization to form the peptidyl TH shown at XI in the figure. The cyclization reaction may be catalyzed by pyridine, suggesting that pyridine may be reacting with the thiocyanate moiety to enhance the reactivity of the reactive carbon center, as has been proposed (Miller, 1988).

Specific reaction conditions for forming an amino acid or peptidyl TH, in accordance with the present invention are given in Examples 1A, 2, 3, and 6 for benzoyl-ITC; in Example 4, for trimethylacetyl-ITC; in Example 5, for ethoxycarbonyl; and in Example 7B; for benzensulfonyl-ITC.

C. Formation and Identification of Amino Acid TH

This section describes the final steps of the method of the invention, which includes (a) treating the peptidyl TH under cleavage conditions effective to cleave the amide linkage joining the TH to the peptide, (b) isolating the amino acid TH released by the cleavage reaction, and (c) identifying the isolated amino acid TH.

A variety of cleavage reaction conditions are known. Hydrolytic cleavage with 12 N HCl, dilute alkali (Kenner), or saturated aqueous triethylamine have been reported. These cleavage reactions are reported to yield up to 70% percent cleavage, but the extreme pH conditions can lead to ring opening and/or damage to internal peptide side chains. More recently, cleavage by treatment with acetohydroxamate in pyridine at pH 8.0 was reported (Meuth). The method affords recovery yields of up to 60-80% of the C-terminal TH (Miller, 1988). A related method involves treatment with primary or secondary amines in acetonitrile.

The cleavage reactions are typically carried out at room temperature or higher, for 15-60 minutes, depending on the cleavage agent used. The course of the reaction can be readily followed, for purposes of optimizing TH release, and minimizing ring opening and damage to the shortened peptide, by examining the integrity of the released amino acyl TH and/or shortened peptide, according to analytical methods described below, during the course of the reaction. Suitable solutions for carrying out the cleavage reaction include a 5-10% solution of trialkyl amine in acetonitrile and a 5-15% solution of tripropylamine in acetonitrile.

In one cleavage method, described in Examples 1, 2, 3, and 4, the peptidyl TH is treated with 10% propylamine in acetonitrile at room temperature for 15 minutes. In a related method, described in Example 5, the peptidyl-TH was cleaved with tetra-N-butyl ammonium hydroxide in water containing 1 mg/ml dithiothreitol (DTT).

Figure 7A:
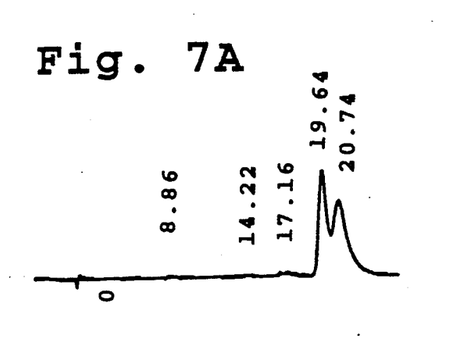
FIGS. 7A and 7B show HPLC chromatograms of Ile-TH formed by reaction of Ile with TMS-ITC in acetic anhydride, according to prior art methods (7A), and by reaction with benzoyl-ITC mixed anhydride reaction, according to the present method.
Figure 7B:
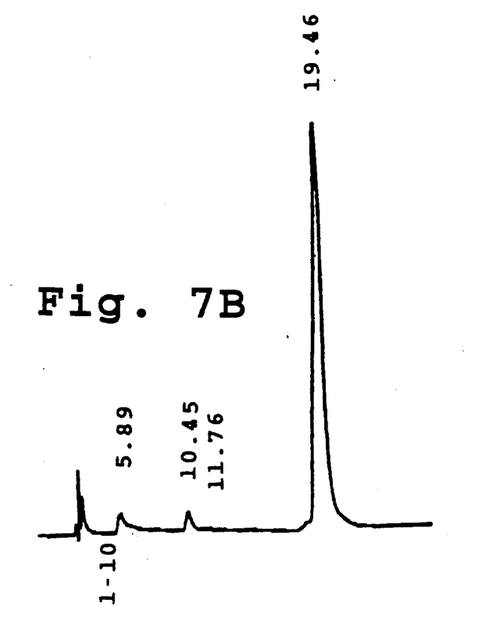

According to one aspect of the invention, it has been discovered that the TH-forming method, when carried out under acidic conditions, preserves the stereoisomeric form of C-terminal amino acid. This is illustrated in Example 6, where t-BOC protected Ile is deprotected with trifluoroacetic acid (TFA), in 25% $H_2O$, to yield a single L-form Ile-TH compound, as seen in FIG. 7B. By contrast, reaction formation of deprotected Ile-TH by reaction with trimethylsilyl isothiocyanate (TMS-ITC), and deprotection (cleavage) with 12N HCl, in accordance with prior-art C-terminal analysis methods (Hawke), produced the two diastereoisomeric forms seen as a doublet in FIG. 7A.

The results of the cleavage reaction are illustrated at the bottom in FIG. 3. In the FIG. 3 reaction, the cleavage produces a peptide shortened by one amino acid (compound XIII) and an amino acid TH XIV whose $R_1$ group is, of course, the amino acid side chain of the original C-terminal amino acid.

The amino acyl TH released from the peptide or the shortened peptide, or both, are analyzed to identify the C-terminal amino acid. Where the peptide is coupled to a solid support, the released TH can be easily separated by removing the cleavage-reaction solvent, e.g., by vacuum centrifugation, and extracting the released TH in a suitable solvent such as acetonitrile, as detailed in Example 1. Where the peptide is free in the cleavage reaction mixture, the mixture may be separated, e.g., by HPLC, as part of the method for identifying the compound.

Figure 5A:
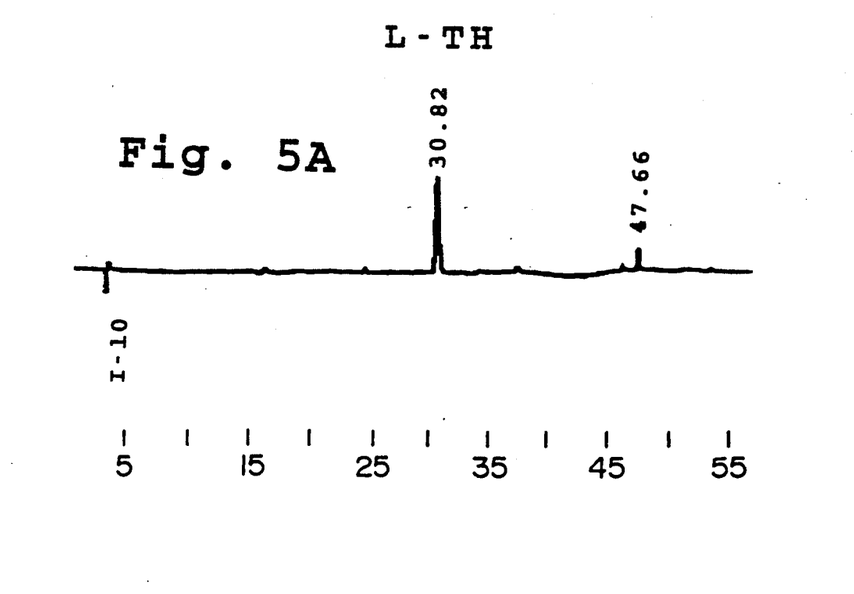
FIGS. 5A and 5B show HPLC chromatograms of amino acid-TH compounds formed for C-terminal leucine (L), and C-terminal methionine (M), respectively.
Figure 5B:
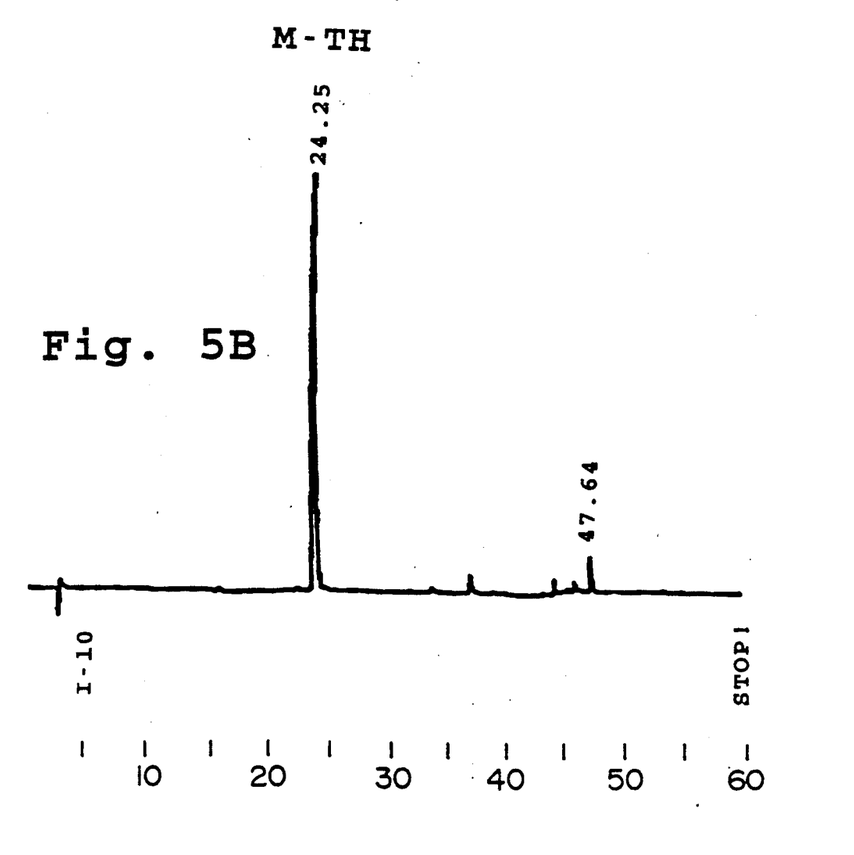

The released amino acid TH compound may be identified by known chromatographic methods, such as high pressure liquid chromatography (HPLC), according to standard procedures. Compound identification can be made conveniently by comparing the retention times in the columns with the retention times of known reference amino acid THs, prepared according to standard methods. The HPLC methods detailed in Example 1 are suitable. FIGS. 5A and 5B, for example, show HPLC profiles of leucine-TH (L-TH) and methionine-TH (M-TH), and FIGS. 6A and 6B, of L-TH and phenylalanine (F-TH).

Alternatively, the released and isolated amino acid TH can be identified by other available tools, such as mass spectrometry or NMR.

D. C-Terminal Amino Acid Sequencing

The method described in Section C above is designed for determining the C-terminal amino acid residue of a peptide. It will be appreciated that repeated application of the method can be used for C-terminal amino acid sequencing of the peptide.

Figure 8:
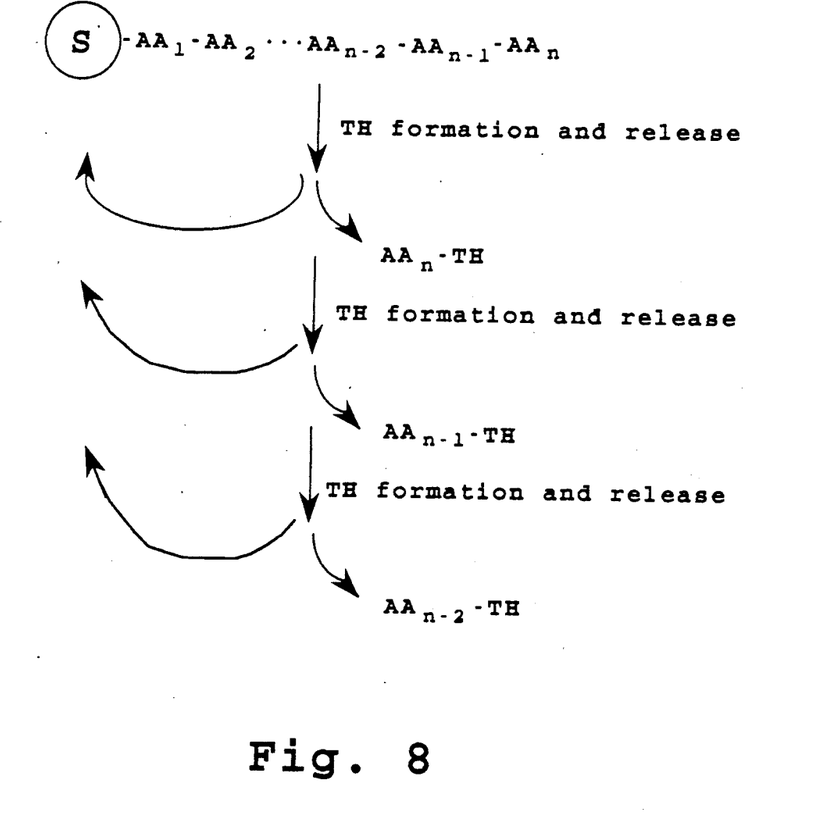
FIG. 8 illustrates the use of the method of the invention for C-terminal peptide sequencing.

FIG. 8 illustrates the sequencing method. The peptide to be sequenced is coupled to a solid support S, as indicated. The peptide is then carried through a first round of steps to (a) produce the C-terminal peptidyl TH, (b) cleave the terminal TH, yielding the C-terminal amino acyl TH ($AA_n$) and a shortened peptide whose C-terminal residue is now $AA_{n-1}$, and (c) identify the released amino acyl TH.

Figure 6A:
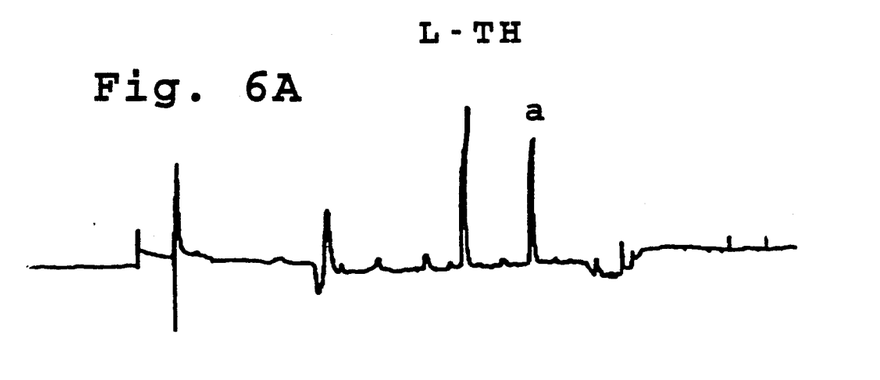
FIGS. 6A and 6B show HPLC chromatograms of the first and second cycles, respectively, in the C-terminal sequencing of the pentapeptide leucine enkephalin (TGGFL)
Figure 6B:
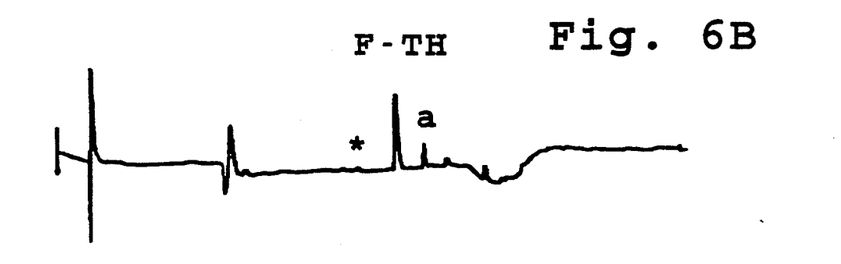

After washing the peptide support, the shortened peptide is treated with a second round of the above steps to release the next-in amino acid as an amino acid TH ($AA_{n-1}$) and yield a peptide shortened by two C-terminal residues. This procedure is repeated until the peptide has been sequenced or until loss of resolution, due to incomplete TH formation and release, makes further sequencing impossible. The sequencing method is illustrated in Example 5, for the determination of the two C-terminal amino acid residues of leucine enkephalin (YGGFL). The HPLC chromatogram from the first round of analysis, shown at 6A shows the C-terminal L-TH peak. The chromatogram from the second round shows the expected F-TH.

The above-detailed technique is easily automated using technology known for the automated sequencing of the N-terminal residues of peptides. One embodiment of a device to automatically sequence a peptide from the C-terminal end employs a solid support contained in a reaction vessel to which fresh solvent and reagents are added, and from which reaction mixtures and solvent washes are removed. The released amino acid TH's are isolated from the stored material for later identification by HPLC.

E. Alternative Mixed Anhydride Reagents

Although the present invention encompasses the mixed anhydrides of carboxylic, carbonic, and sulfonic acid described in Section A, additional mixed anhydrides as disclosed below may be suitable for forming C-terminal amino acid-TH compounds.

One of the alternative reagents is a carbamate mixed anhydride of isothiocyanic acid, having the general formula:

where R may be any amine, and preferably a quarternary amine, such as trimethyl amine. This reagent would be expected to have about the same electronegativity as the carbonate mixed anhydrides, and thus should provide a reasonable yield of the desired peptidyl-TH product.

Figure 9:
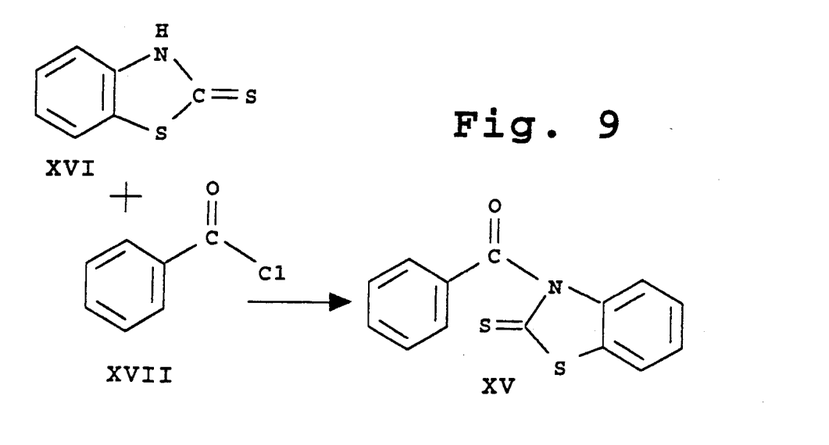
FIG. 9 shows the synthesis of a mercaptobenzothiazole compound which may be used used for generating C-terminal amino acid-phenyl TH derivatives.

Another alternative mixed anhydride is a benzoyl-mercaptobenzothiazole (MBT) XV, such as illustrated at the right in FIG. 9. This compound may be prepared according to the synthetic method described in Example 8. Briefly, MBT XVI is dissolved in a dry, inert solvent in the presence of a suitable base, such as diisopropyl ethyl amine. A selected acyl chloride, e.g., benzoyl chloride XVII, is then slowly added at a reduced temperature to form the desired product. Related acyl MBT compounds, such as acetyl MBT, can be prepared by a similar method, using the desired acyl chloride starting material.

Figure 10:
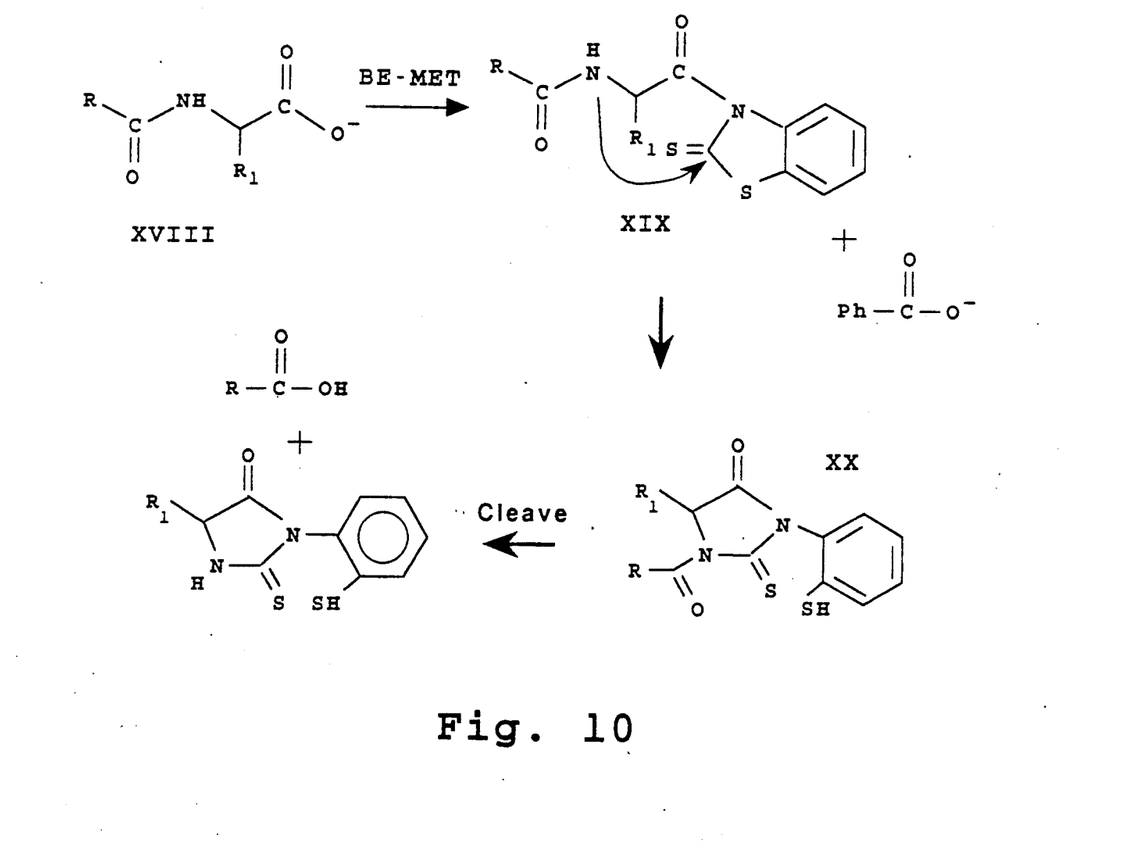
FIG. 10 illustrates the proposed reaction of a mercaptobenzothiazole compound with a C-terminal amino acid, and subsequent cleavage to form the amino acid-phenylTH compound.

FIG. 10 shows the proposed reaction steps in the formation of a peptidyl phenyl TH, employing an MBT reagent. The reaction conditions may be substantially similar to those described in Section B, with suitable adjustment in reaction time, if necessary, to ensure completion of the TH-formation reaction. Typical reaction conditions are given in Example 8.

With reference to FIG. 10, the deprotonated peptide (XVIII) is reacted with benzoyl-MBT (BzMBT) to form, in the proposed reaction pathway, the intermediate peptide benzothiazole compound indicated at XIX. The formation of the intermediate may proceed via an activated anhydride, with subsequent attack by a benzathiazole ion, or may involve a concerted rearrangement reaction, as discussed with reference to FIG. 2.

The cyclization of the intermediate benzathiazole to form the peptidyl aryl TH likely proceeds along the same pathway as described in FIG. 3, with the electrophilic thio ring carbon reacting with the amide nitrogen, followed by cyclization to form the desired peptide phenyl TH compound XIV.

Still another possible mixed anhydride is a mixed anhydride of isocyanic acid and carboxylic acid, such as benzoyl isocyanate. Such a reaction, which is described in Example 9, produces a reasonable yield of the desired amino acid-TH product, as reported in the example.

From the foregoing, it can be appreciated how various objects and features of the invention are achieved. The method of the invention permits peptidyl TH formation under substantially milder conditions than prior-art methods relying on anhydride activation of the peptide's carboxyl group. At the same time, the TH-formation reaction can be carried out relatively rapidly, e.g., 15–30 minutes, thus allowing sequencing to be carried out quickly in an automatic system.

In addition, when the cleavage reaction in the method is carried out under acidic conditions, the method preserves the stereochemistry of the C-terminal amino acid, and thus can be used to determine L- or D-form amino acids.

The following examples are intended to illustrate the synthesis of various acyl compounds, and their use in determining C-terminal amino acid groups, and for C-terminal sequencing. The examples are in no way intended to limit the scope of the invention.

Materials

Pyridine was used as supplied from Aldrich, as was mercaptobenzothiazole, propylamine and triethylamine. Benzoyl isothiocyanate was from Aldrich, as supplied or vacuum distilled. Leucine enkephalin was from Sigma, dipeptides were from Bachem Biosciences. Polydimethyl acrylamide resin was prepared according to J. Sparrow, and had about 0.7 meq/g of amino groups. Conversion of those amino groups to isothiocyanates was performed using thiocarbonyl diimidazole and diisopropylethyl amine (DIPEA) in acetonitrile. Nuclear magnetic resonance spectra were collected on a Jeol FX90 spectrometer. Mass spectral analyses were performed by the Berkeley Mass Spectrometry Laboratory under the direction of Dr. J. Leary.

Peptides were attached to resin in one of two ways: (1) by a urea linkage, or (2) by a thiourea linkage (using isothiocyanato-resin, above).

(1) Urea link: The resin is neutralized with excess DIPEA and allowed to react with excess DSC in 10% pyridine/NMP for 1-2 hours at ambient temperature. After several washes, finally with ACN, a solution of the peptide in 10% pyridine/water is added to the moist resin and allowed to stand overnight. The resin is washed extensively and dried under vacuum. Typical loading is >100 nanomoles/ml. Confirmation is by amino acid analysis, and one round of C-terminal analysis.

(2) Thiourea link: A solution of the peptide is added to either ITC (above) or DITC resin, and incubated at 45° C. overnight. After rinsing and drying, attachment is confirmed by TFA cleavage of the peptide (less the aminoterminal amino acid) from the resin followed by characterization on HPLC and by sequence analysis.

EXAMPLE 1

C-Terminal Analysis of a Leu-Val Dipeptide

A. Coupling

Peptidyl resin (about 1 mg, Leu-Val attached via a urea-linkage) was suspended in 100 $\mu$l of 10% pyridine/acetonitrile (PA). Benzoyl isothiocyanate (BITC) (10 $\mu$l) was added, mixed by agitation, and allowed to react for 30 minutes at 60° C. The resin was extensively washed with several volumes of acetonitrile, and dried under vacuum.

B. Hydrolysis

The resin from above was wetted with 10 $\mu$l of 10% propylamine in acetonitrile. After 15 minutes at room temperature volatiles were removed and the amino acid TH extracted with acetonitrile for analysis.

C. HPLC

The separation of the hydrophobic amino acid thiohydantoins was readily achieved on a narrow-bore system (Model 120A, Applied Biosystems) using a PTH-C18 column (2.1 mm×22 cm, ABI) and a TFA-water-acetonitrile gradient system. The column was first equilibrated in A solvent (0.1% TFA in water, v/v), held in 100% A, 0% solvent B for 5 minutes after injection, then a linear gradient was developed to 40% B solvent (0.85% TFA in 70% acetonitrile) over 30 minutes. The percentage of B was then increased to 90% over 5 minutes, and held there for 20 minutes. The flow rate was 200 $\mu$l/ min at ambient temperature. Effluent was monitored at 269 nm for TH, and 214 nm for peptides.

Figure 4A:
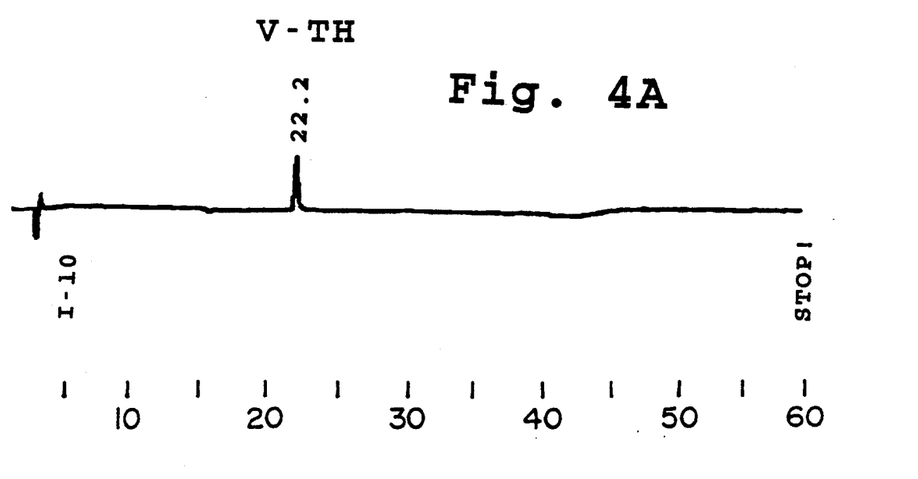
FIGS. 4A and 4B are HPLC chromatograms showing the comparitive yields of C-terminal amino acid-TH formed in a method which uses TMS-ITC in acetic anhydride, according to prior art methods (4A), and a benzoyl-ITC mixed anhydride reagent, according to the present invention (4B)
Figure 4B:
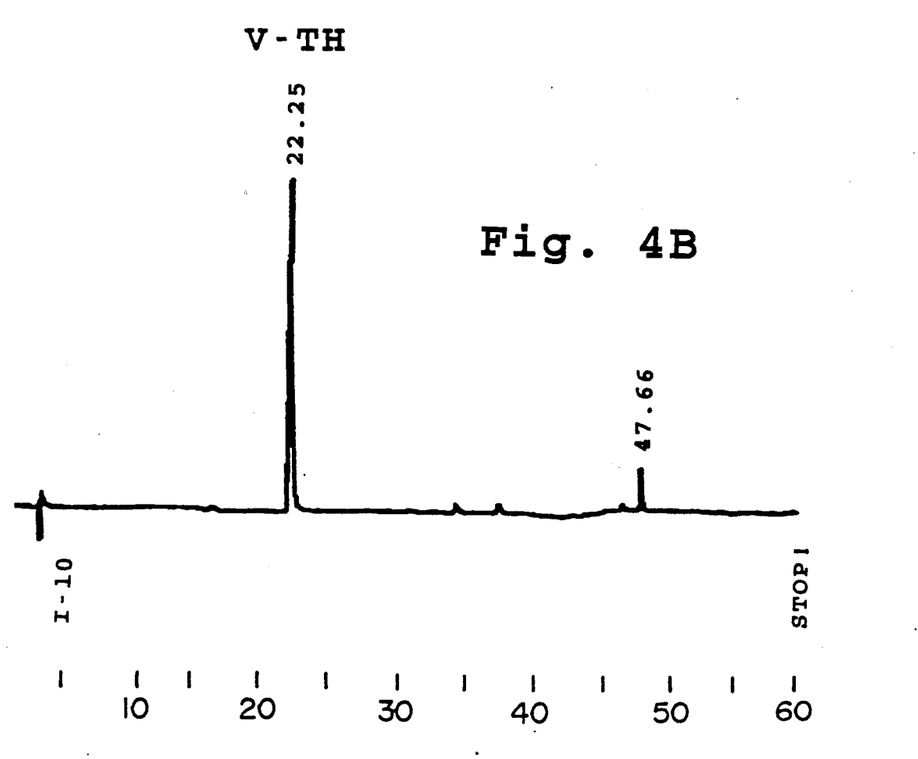

The thiohydantoin is identified by comparison with the elution of authentic material (part D, below). The HPLC of the extract in part B is shown in FIG. 4B. The major peak is readily identified as TH-V. The assignment was confirmed by coinjection. FIG. 4A shows the TH-V product generated in a control experiment in which the resin was reacted with trimethylsilyl isothiocyanate (Hawke), in the an anhydride activating reagent.

D. Preparation of Authentic Standards

Amino acid thiohydantoins of the hydrophobic residues are preparable by classical methods (such as Cromwell). Briefly, the amino acid is treated with a thiocyanate salt in acetic acid/acetic anhydride at up to 90° C. for 30 minutes. After vacuum drying, the residue is taken up in 12 N HCl and allowed to stand at room temperature for up to 1 hour. The mixture is again vacuum dried, and the residue recrystallized, usually from boiling water. The structures were consistent by NMR and mass spectrometry.

EXAMPLE 2

C-Terminal Analysis of A-M Dipeptide

Following the procedures described in Example 1, immobilized Ala-Met (urea linkage) was degraded for one cycle using BITC and PA. The assignment of methionine TH was confirmed by coinjection.

EXAMPLE 3

Leucine Enkephalin C-Terminal Analysis

Leu-enkephalin (YGGFL) linked through a thiourea linkage to resin was treated with BITC and PA as in Example 1. The released L-TH was detected by HPLC.

The resin was further rinsed with acetonitrile and dried, then treated with 25% TFA in water at 60° C. for 10 minutes to release the peptide components from the resin. HPLC analysis followed by isolation and both sequencing and FAB mass spectrometry showed a major peak corresponding to the desleucine peptide, confirming the loss of the C-terminal amino acid.

EXAMPLE 4

C-Terminal Analysis of N-Protected Phe Gly

N-protected t-Boc Phe-Gly was obtained commercially. The peptide was suspended in 100 $\mu$l of 10% pyridine/acetonitrile (PA). Trimethylacetyl ITC (10 $\mu$l) was added, mixed by agitation, and allowed to react for 30 minutes at 60° C. The resin was extensively washed with several volumes of acetonitrile, and dried under vacuum.

Cleavage of both the t-Boc group and the Gly-TH was achieved by heating at 60° in 25% TFA/water. The reaction, as followed by HPLC, showed rapid loss of starting material (judged after 15 minutes of reaction), along with the appearance of G-TH and a minor component (probably the Boc-deprotected dipeptidyl-TH). After two hours reaction, only G-TH was detectable.

EXAMPLE 5

C-Terminal Analaysis of Leu-Enkephalin

Immobilized leucine enkephalin (urea linkage) was degraded for two cycles of chemistry. The couplings were performed with ethoxycarbonyl isothiocyanate (instead of BITC) for 5 minutes at 60° C. Cleavages were effected by adding 10 $\mu$l of 10% tetra-N-butyl ammonium hydroxide in water containing 1 mg/ml DTT to the dry resin, and heating for 45 minutes at 60° C. Chromatograms are shown in FIGS. 6A and 6B. The cycles were assigned as leucine and phenylalan respectively. The assignments were confirmed by coinjection.

EXAMPLE 6

Preparation of Single Isomer of Isoleucine

Approximately 10 $\mu$moles of t-Boc-isoleucine was dissolved in 100 $\mu$l 1 10% pyridine/acetonitrile. This was heated with 10 $\mu$l BITC at 60° for 20 minutes. HPLC analysis of the product showed a single major new peak, the t-Boc-Ile-thiohydantoin. A small portion of this mixture was cleaved in 25% TFA at 60° C. for 10 minutes. The reaction mixture was diluted with acetonitrile and analysed by HPLC. The result was a single peak corresponding to Ile-TH. Running the peak isocratically (11% B) gave an improved resolution of isomers, shown in FIG. 7B, and allows estimation of the upper bound of about 2% epimerization.

T-Boc-isoleucine (10 $\mu$mol) was dissolved in 100 $\mu$l 10% TMS-ITC in acetic anhydride. The reaction was heated at 60° for 20 minutes. The material was cleaved in 25% TFA at 60° C. for 10 minutes, and the reaction mixture was diluted with acetonitrile and analysed by HPLC., as above. The result was a doublet peak, corresponding to the diasteromeric forms of Ile-TH, as seen in FIG. 7A.

EXAMPLE 7

Reaction of Sulfonyl ITC Reagent with N-Protected Amino Acid

A. Preparation of benzenesulfonyl isothiocyanate (BzS-ITC)

Benzenesulfonyl chloride was obtained from Aldrich Chemical Co. The compound (1 mmol) was dissolved in 10ml CH₂Cl₂ with 2 mmol pyridine ethyl amine to a final volume. To this mixture was added 1 mmol of TMSITC, and the reaction mixture was stirred for 1 hour at 25° C. The benzylsulfonyl isothiocyanate (BzSITC) was recovered by filtering the salrts which formed, and removing the solvent and volatile sideproducts by vacuum.

B. Reaction to form amino acid TH

One mmol of t-Boc-Leu was dissolved in dichloromethane containing pyridine, and 1 mmol of BxSITC prepared as in A. After reacting overnight, the solvent was removed by rotary evaporation and the t-Boc-Leu-TH which formed was purified by chromatography on silica gel. The identify of the TH compound was confirmed by NMR and HPLC.

EXAMPLE 8

Reaction of bZ-MBT with Peptidyl Resin

A. Preparation of BzMBT

Mercaptobenzothiazole (1 mmole) and diisopropyl ethylamine (1 mmole) were dissolved in 5 ml acetonitrile. Benzoyl chloride (1 mmole) was added slowly by syringe while stirring rapidly. After 2 hours at room temperature solvent was partially removed to permit precipitation of the amine salt. The supernatant was further concentrated, and chromathographed on silica get (9:1, heptane:ethyl acetate).

B. Reaction

Peptidyl resin (1 mg Lenk, thiourea linkage) was suspended in 100 μl of 10% pyridine in acetonitrile containing 1 mg Bz-MBT. The reaction was heated at 60° C. for 30 minutes, then washed and dried as before. The arylthiohydantoin was cleaved with 10% propylamine at room temperature for 15 minutes. Treatment with TFA released the remaining peptide fragments from the resin, as confirmed by the loss of the C-terminal residue as assessed by HPLC.

EXAMPLE 9

Reaction with Benzoyl Isothiocyanate

One mole of t-Boc-Leu was reacted with a slight excess of benzoyl isothiocyanate in a reaction mixture similar to that in Example 7. The t-Boc-Leu-TH was chromatographed, then deprotected to give a moderate yield of hydantoin, as confirmed by NMR.

IT IS CLAIMED:

1. A method of determining the C-terminal amino acid residue of a peptide, comprising reacting the peptide with a mixed anhydride of isothiocyanic acid and an acid selected from the group consisting of carboxylic, carbonic, and sulfonic acid, under basic conditions in which the C-terminal acid group of the amino acid is deprotonated, to form a peptidyl thiohydantoin in which the C-terminal amino acid has been converted to a C-terminal amino acid thiohydantoin which is linked to the next-in amino acid in the peptide through an amide bond, treating the peptidyl thiohydantoin under conditions effective to cleave said amide bond, thereby releasing a C-terminal amino acid thiohydantoin and a reduced-length peptide, and identifying the released amino acid thiohydantoin.

2. The method of claim 1, wherein said mixed anhydride has the form:

where R is an alkyl or aryl group.

3. The method of claim 2, wherein said mixed anhydride is a benzoyl isothiocyanate.

4. The method of claim 1, wherein said mixed anyhydride is an alkyl acylisothiocyanate.

5. The method of claim 1, wherein said reacting is carried out in the presence of pyridine.

6. The method of claim 1, wherein said reacting is carried out at a temperature between about 50°–70° C., for a reaction time between about 10 and 60 minutes.

7. The method of claim 1, wherein said treating is carried out in a 5–10 % solution of trialkyl amine in acetonitrile.

8. The method of claim 1, wherein said treating is carried out in a 5–15 % solution of tripropylamine in acetonitrile for about 15 minutes at room temperature.

9. The method of claim 1, wherein said peptide is attached at a non C-terminal residue to a solid support, and which further includes repeating said reacting, treating and identifying steps one or more times to identify the sequence of amino acids in the peptide, from the C-terminal peptide end.

10. The method of claim 9, which is carried out in an automated fashion, by alternately and successively exposing the solid support to (i) a fresh solution of the mixed anhydride in a basic solution, and (ii) fresh treating solution, and isolating the amino acid released into each successive treating solution.

11. A method of producing a thiohydantoin (TH) of a protected amino acid having a free carboxylic acid group, comprising contacting the amino acid in solution with a mixed anhydride of isothiocyanic acid and carboxylic, carbonic or sulfonic acid, under basic conditions in which the carboxylic acid group of the amino acid is deprotonated, and by said contacting, forming the TH of the amino acid in solution.

12. The method of claim 11, wherein the mixed anhydride has the form:

where A is an alkyl, alkoxyl, aryl or aryloxy group.

13. The method of claim 11, wherein said contacting is performed in the presence of pyridine.

* * * * *